US005773290A

United States Patent [19]
Gould et al.

[11] Patent Number: 5,773,290
[45] Date of Patent: Jun. 30, 1998

[54] MAMMARY GLAND-SPECIFIC PROMOTERS

[75] Inventors: Michael N. Gould; Kai-Shun Chen, both of Madison, Wis.

[73] Assignee: Wisconsin Alumni Research Foundation, Madison, Wis.

[21] Appl. No.: 726,725

[22] Filed: Oct. 7, 1996

[51] Int. Cl.$^6$ ............................ C07H 21/04; C12N 15/70
[52] U.S. Cl. ...................................... 435/320.1; 536/24.1
[58] Field of Search .................................. 536/23.1, 23.5, 536/24.1; 435/320.1

[56] References Cited

PUBLICATIONS

Bundgaard, J. et al. 1994, Biochemical and Biophysical Research Communications vol. 202 No. 3 pp. 1468–1475.

J. Drouin, et al., "Glucocorticoid receptor binding to a specific DNA sequence is required for horomone–dependent repression of pro–opiomelanocortin gene transcription," *Molec. Cell. Biol.* 9(12):5305–5314, 1989.

E. Garay–Rojas, et al., "An apparent autocrine mechanism amplifies the dexamethasone– and retinoic acid–induced expression of mouse lipocalin–encoding gene 24p3," *Gene* 170:173–180, 1996.

S. Hraba–Renevey, et al., "SV40–induced expression of mouse gene 24p3 involves a post–transcriptional mechanism," *Oncogene* 4:601–608, 1989.

S. Li and J. Rosen, "Glucocorticoid regulation of rat whey acidic protein gene expression involves hormone–induced alterations of chromatin structure in the distal promoter region," *Molec. Endocrin.* 8(10): 1328–1335, 1994.

A. Ray and K. Prefontaine, "Physical association and functional antagonism between the p65 subunit of transcription factor nf–κb and the glucocorticoid receptor," *Proc. Natl. Acad. Sci. USA* 91:752–756, 1994.

D. Sakai, et al., "Hormone–mediated repression: a negative glucocorticoid response element from the bovine prolactin gene," *Genes & Dev.* 2:1144–1154, 1988.

B. Stein and M. Yang, "Repression of the interleukin–6 promoter by estrogen receptor is mediated by NF–κB and C/EBPβ," *Molec. Cell. Biol.* 15(9):4971–4979, 1995.

S. Stoesz and M. Gould, "Overexpression of neu–related lipocalin (NRL) in neu–initiated but not ras or chemically initiated rat mammary carcinomas," *Oncogene* 11:2233–2241, 1995.

M. Truss, et al., "Interplay of steroid hormone receptors and transcription factors on the mouse mammary tumor virus promoter," *J. Steroid Biochem. Molec. Biol.* 43(5):365–378, 1992.

D. White, et al., "Structure and chromosomal localization of the human gene for a brain form of prostaglandin $D_2$ synthase," *J. Biol. Chem.* 267(32):23202–23208, 1992.

*Primary Examiner*—James Ketter
*Assistant Examiner*—Irem Yurel
*Attorney, Agent, or Firm*—Quarles & Brady

[57] ABSTRACT

An isolated DNA fragment comprising a mammary gland-specific promoter is disclosed. Preferably, this promoter promotes gene expression throughout the estrous cycle in a constant manner. In one embodiment, the promoter comprises nucleotides 1154 through 2967 of SEQ ID NO:1 or 1102 through 2910 of SEQ ID NO:2.

13 Claims, 9 Drawing Sheets

```
         1                                                                                        80
hPGDS2  ..CTCCTCCT  GCACACCTTC  CGCACACCTC  CCTCGCTCTC  CCACACCACT  GGCACCAGGC  CCCGCACACC  TGCTCGGCTG
rPGDS2  ..........  ..........  ..........  ..........  ..........  ...CCTCAGG  CTCAGACACC  TGCTCTACTC
 rNRL   ..........  ........CT  CTTCCTCCTC  CGGCACACAT  CGGACCTAGT  AGCTGCTGAA  ACCATGGGCC  TGGGTGTCCT
hNGAL   CACGAGTCCA  CCCCTGCCAG  GCCCAGCAGC  CACCACAGCG  CCTGCTTCCT  CGGCCCTGAA  ATCATGCCCC  TAGGTCTCCT

81                                  EXON 1                                              160
hPGDS2  CAGGAGAATG  GCTACTCATC  ACACGCTGTG  GATGGGACTG  GTCCTGCTGG  GGCTGCTGGG  CGGCCTACAG  GCAGCACCCG
rPGDS2  CAAGCAAATG  GCTGCTCTTC  CAATGCTGTG  GACCGGGCTG  GTCCTCTTGG  GTCTCTTGGG  ATTTCCACAG  ACCCCAGCCC
 rNRL   GTGTCTGGCC  CTTGTCCTGC  TTGGGGTCCT  GCAGAGGCAG  GCCCAGGACT  CAACTCAGAA  CTTGATCCCT  GCCCCACCTC
hNGAL   GTGGCTG...  CCTAGCCTGT  TGGGGGCTCT  GCATGCCCAG  GCCCAGGACT  CCACCTCAGA  CCTGATCCCA  GCCCCACCTC

161                                            ▼                                        240
hPGDS2  AGGCCCAGGT  CTCCGTGCAG  CCCAACTTCC  AGCCGGACAA  GTTCCTGGGG  CGCTGGTTCA  GCGCGGGCCT  CGCCTCCAAC
rPGDS2  AGGGCCATGA  CACAGTGCAG  CCCAACTTTC  AACAAGACAA  GTTCCTGGGG  CGCTGGTACA  GCGCGGGCCT  CGCCTCCAAT
 rNRL   TGATCAGTGT  GCCCCTGCAG  CCAGGCTTCT  GGACCGAACG  GTTCCAGGGC  AGGTGGTTCG  TTGTCGGCCT  GGCAGCGAAT
hNGAL   TGAGCAAGGT  CCCTCTGCAG  CAGAACTTCC  AGGACAACCA  ATTCCAGGGG  AAGTGGTATG  TGGTAGGCCT  GGCAGGGAAT

241                                  EXON 2                                             320
hPGDS2  TCGAGCTGGC  TCCAGGAGAA  GAAGGCAGCG  CTGTCCATGT  GCAAGTCGGT  GGTGGCCCCT  GCGGCGGATG  GTGGCTTCAA
rPGDS2  TCAAGCTGGT  TCCGGGAGAA  GAAAGAGCTA  CTGTTTATGT  GCCAGACAGT  GGTAGCTCCC  TCCACAGAAG  GCGGCCTCAA
 rNRL   GCGGTC...C  AGAAAGAAAG  ACAAAGCCGC  TTTACCATGT  ACAGCACCAT  CTATGAGCTA  CAGGAAGACA  ATAGCTACAA
hNGAL   GCAATT...C  TCAGAGAAGA  CAAAGACCCG  CAAAAGATGT  ATGCCACCAT  CTATGAGCTG  AAAGAAGACA  AGAGCTACAA

321                   ▼                                             EXON 3              400
hPGDS2  CCTGACCTCC  ACCTTCCTCA  GGAAAAACCA  GTGTGAGACC  CGAACCATGC  TGCTGCAGCC  CGGGGACTCC  CTCGGCTCCT
rPGDS2  CCTCACCTCT  ACCTTCCTAA  GGAAAAACCA  GTGTGAGACC  AAGGTGATGG  TACTGCAGCC  GGCAGGGGTT  CCCGGACAGT
 rNRL   CGTCACTTCC  ATCCTCGTCA  GGGGCCAGGG  CTGTCGCTAC  TGGATCAGAA  CATTCGTTCC  AAGCTCCAGG  CCTGGCCAGT
hNGAL   TGTCACCTCC  GTCCTGTTTA  GGAAAAAGAA  GTGTGACTAC  TGGATCAGGA  CTTTTGTTCC  AGGTTGCCAG  CCCGGCGAGT

401                         ▼                                                           480
hPGDS2  ACAG......  ...CTACCGG  AGTCCCCACT  GGGGCAGCAC  CTACTCTGTG  TCAGTGGTGG  AGACTGACTA  CGACCACTAC
rPGDS2  ACAC......  ...CTACAAC  AGCCCCCACT  GGGGCAGCTT  CCACTCCCTC  TCAGTGGTAG  AAACCGACTA  CGATGAGTAC
 rNRL   TCACCCTGGG  GAATATTCAC  AGCTACCCTC  AGATACAGAG  CTACGATGTG  CAAGTGGCCG  ACACTGACTA  CGACCAGTTT
hNGAL   TCACGCTGGG  CAACATTAAG  AGTTACCCTG  GATTAACGAG  TTACCTCGTC  CGAGTGGTGA  GCACCAACTA  CAACCAGCAT
```

FIG. 1A                                    ▼ EXON-INTRON-EXON SPLICING SITE

TO FIG. 1B

```
                                    FROM FIG.1A
                   _____/_____
        481                          EXON 4              ▼           560
hPGDS2  GCGCTGCTGT ACAGCCAGGG CAGCAAGGGC CCCGGCGAGG ACTTCCGCAT GGCCACCCTC TACAGCCGAA CCCAGACCCC
rPGDS2  GCATTCCTGT TCAGCAAGGG CACCAAGGGC CCAGGCCAGG ACTTCCGCAT GGCCACCCTC TACAGCAGAG CCCAGCTTCT
 rNRL   GCCATGGTAT TTTTCCAGAA GACCTCTGAA AACAAACAGT ACTT...CAA AGTCACCCTG TACGGAAGAA CCAAGGGGCT
hNGAL   GCCATGGTGT TCTTTAAGAA AGTTTCTCAA AACAGGAGT  ACTT...CAA GATCACCCTC TACGGGAGAA CCAAGGAGCT

561                          EXON 5                              640
hPGDS2  CAAGGCTGAG TTAAAGGAGA AATTTACCGC CTTCTGCAAG GCCCAGGGCT TCACAGAGGA TTCCATTGTC TTCCTGCCCC
rPGDS2  GACGGAGGAA CTGAAGGAGA AATTCATCAC CTTTAGCAAG GACCAGGGCC TCACAGAGGA GGACATTGTT TTCCTGCCCC
 rNRL   GTACGATGAA CTGAAGGAGC GATTCGTCAG CTTTGCCAAG TCTCTGGGCC TCAAGGATAA CAACATCGTT TTCTCTGTTC
hNGAL   GAATTCGGAA CTAAAGGAGA ACTTCATCCG CTTCTCCAAA TCTCTGGGCC TCCCTGAAAA CCACATCGTC TTCCCTGTCC

641  ▼      EXON 6      ▼                       EXON 7          720
hPGDS2  AAACCGATAA GTGCATGACG GAACAATAGG ACTCCCCAGA GCTGAAGCTG GGACCGCAGC CAGCCAGGT. .....GACCC
rPGDS2  AACCGGATAA GTGCATTCAA GAGTAAACAC AGGTGAGAGA AGTCAGTCAC AGGTAACACA TGGTGATGT. .....GGCCT
 rNRL   CCACCGACCA ATGCATTGAC AACTGAACAG ACGGTGAGCG TGGCTGACTG GGATGTGCAG TGGCCTGATG GTTCAGGTCC
hNGAL   CAATCGACCA GTGTATCGAC GGCTGAGTG. .......... .......... .......... .......... ..........

751                                                              800
hPGDS2  CTGCGATCTG GATGTTTCCG CTCTGTTCCT TCCCCGAGCC CCTGCCCCGG CTCCCCGCCA AAGCACCCCT GCCCCTCGG
rPGDS2  CAGGACTC.. ........CCG TGCTCTGTCA CTCTTGAGAC CCAAGCCCTG ..GCTCCCCA AAGACCTTCT CCGCCCTCCA
 rNRL   CACCTGTCTG TCTGCCGCTC CATCTTTCCT GTTGCCAGAG AATCACCTGG CTGCCCCACC AGCCATGATT CCATCAAGCA
hNGAL   .......... .......... .......... .......... .......... .......... .......... ..........

801                                                              880
hPGDS2  GCTTCCTCCT GGCTCTGCGG AATAAACTCC GGAAGCAAGT CTGT...... .......... .......... ..........
rPGDS2  GCTTTGCCTT GG...TGGAG AAATAAAATC CAAAGCAAGT C......... .......... .......... ..........
 rNRL   TCTGATCCCT CTTATTTGAT CAGCTCTCCC CATCCACCTG TGTTAACGCT GCCCCACCAA CGGGCTCCCC CTTTCTGCTG
hNGAL   .......... .......... .......... .......... .......... .......... .......... ..........

891            900
hPGDS2  .......... ..........
rPGDS2  .......... ..........
 rNRL   AATAAACACA TGTCCCCAAA
hNGAL   .......... ..........
```

FIG. 1B

▼ EXON-INTRON-EXON SPLICING SITE

```
-2967 GAATTCCGCA AGCAGACCTG AGGGCCAGGC TGGAGAGTGG AGCTGCGTTC GCTCCAGCCC CTCAAGGCCA GGCTCACCAG TTTCTGCAGT GAGTTTCTGG

-2867 ATCAGAATGT CAGACTGGAT TCTTGAAATG CAGTAACCTC GGAGCCTCTC ATGTGGAATG GACCTAGGTC GGGTTGTGTA GCAGTTAGAG TTCTTGGGCT

-2767 TTATGACCAC AGAAAACTCA AGTGTGACCT AGATGTGTTA CTACTAAGTT CAGGGTCAGC ACAGATTACA CAATGAGACC TCATATCAAA ATAAATAATA
                                    ←─────                           ─────→
                                     1/2 ERE                         1/2 ERE
-2667 AATAATAAAA AGAAGTAGCG GGGGCTGGGG ATTTAGCTCA GTGGCAGAGC GCTTACCTAG GAAGCGCAAG GCCCTGGGTT CGGTCCCCAG CTCCGAAAAA

-2567 AAAAAGAAAA AAAAAAAAAA AAAAAAAGAA GTGGCTGGCT TGGTTGGCGA TGTGTGCCAA CACTCAGAGG TAGAATCAAG AGAACAAGGG AAGGAAGGAA

-2467 GAGGGAGGAA GGAAGGGAAG GAGGGAGGAA GGAAGAAGAA GGGAGGGAGG GAAGAAGGAG GTGGGAGGAA GGAAGGAAAG AAGGAAAGAG ACCGACTGGA

-2367 CGAGAGGTGG AGGCAGGGGG ATGAGAAGTT CAAAGTCATC TTTGGTGACA TAGGGAGTTT GAGGCTACCT GGCCTTTAGG GATTCAGTTT CAGAGAGAGA

-2267 GGGTTCATGG GAGAGCTGGC AGGATCCTGG GGGAAGAATC AGCAGGCTGA AGGTGGCTGT GTGCCTTGTA CCTGGAACAG CCAGGGTCCT GAGCTAGGCC

-2167 ATCTCCCCTC CCACCCTTAA TTCTGACCTT TTAGTTTTTC CAGACCCAGC TCTCTGCCCC AGTTCATACT GGCTCGGTTC CACTGGTCAC TCTGCCCCCT
                            ←─────
                             1/2 ERE
-2067 GGTTTTCAGA GTCTAGAATA TCCTGCCTGT CCAGCTCCTC TGAGATTCTG GTCTCTGTTT TTCCTGACTA AAAATTCTTG GGGGCTCTGT CTACACCCAA
                                                                                                          CAAT BOX
-1967 TAATCACCAG AGACTCAAGG GTGCCTTTGA TTTATACATG AGTTTGTTTG TTTTAAGTCA AAGGCCTTGA GTGTATCCTT TGGCTTGCTT GCCTCAAACT
       ─────→
-1867 CCCAATGCAG ACCAGGCTCA TCTGGCCTTG AAGTCACAGA GATCCTTTGC CTCTGCACAG AGTGTTGGGC TTAAAGGTGG GAGCCACCAC ATACAGCTTT
       CAAT BOX
       ─────→
-1767 CAAGGAGACC TTTCAAGCTA ACGTGTTTAG TTGGAAGGTT GGTTCTTTGT ACTGTTGGAA ATAGAATTTG GGGCCTCCCA CGTGCTAGAC AAACCCTCCA
                                                                                                  1/2 ERE
                                                                                              ─────→
-1667 CCATGGAGCT CTATTCCTCA GTTCTTGGAT ACCTTTTAAG GTCACAGAGG GTAGAAGGGG TGGATCCCCT AGGTCTGAGC TACAAGGGGC TGGAAGGGTG
                                                  ─────────nGRE/nPRE─────────
-1567 GGAGGTCCCT GGTACCTCAA GAGTGACAGG CTCGGTGGC CACATTGTCC CCACAGCTTG GCTCAGCTTC ACTTCCTGTC CTTTCATCAT CCAGGGACCT
```

FROM FIG. 2A

```
-1467 GAGGGGACAG ATTGTAGCGC TGTAGTCTTT CTGACATGGG AGAGGGGGAA GGCTGCATCC TAGGTGTGGG GGGATGTGAG GCTATAGCCT ACTTATCAGG

-1367 TTAAAATCCC CCTCTAAGCT TTCCCTCCTG GCTAACCACC CTGAGCTAAG CAGCAGTGGA AGGGGGAGGT CAGGAGCAGC AAACAGATCA ATAAGCCTTT
                                                                1/2 ERE                      1/2 ERE
-1267 TTAGTCCTGT GCAGGGCCAG AGGACTTCAG TCCAGCCTTA GGTCAGATGT TCAGATGCGG ATTCTGAGGA AGCCACCTGG CGGGGAGGGA AGCACAATAT
                                                    nGRE/nPRE (POMC)
-1167 AGCATCTGGG ATCCATCCAT CGCAACCTTT CAATGAATGT TAGCCAGGCC CCAGAGAGGA AAGGGCTTTT TTTTCAGCCC TAGGCTGGAA TCAGCTGGGG

-1067 AGAGAAAGTC CTAAGGCTGG GGCACTAAGT TCTCCTGCTC AAGGCTATGG CCAGAGACAG GGGGATGCCT TTTCTTTTCT TTTCTTTTTT CTTTTTTTTT

-967  TTTTTTTTTT TTTTTTGGTT CTGTTTTTCG GAGCTGGGGA CCAAACCCAG GGGATGCCTT TTCAAGGGAG GATAACTTAA GGAGAAGGTG GAACCTTGCT

-867  TCTGTCCAAA GTAACTGGAG TACACTGGGC AGTTTGGACA CACACACACA CACACACACA CACACACACA CACCCCTACT TTTCCCAAGG GGCTGGTGCT
                                                            CA REPEAT
-767  CCCCCTTATC CTACGATGAC AACAAGGTTG CAAGTCCTTG CCTTTGAAAG TGGCTGTATT CTAAGGACCG TGTGGCACAG GAGAGGGGTT GTCCCTGAGA

-667  GTTCAACTGC TGCCCTGTCT GCTCCTGTAA ATGTCAGCAT GGTCATGGGA AAGCAAAGGG GCTCAAGGGA TTGGGCACCT CCAGGCTAAT CTTCTGGCTG
                                 OCTAMER                                                    CAAT BOX
-567  CCTCACCCTG TGCCAGGACC AAGTCCAAGC TTGACAGGCT TGGAACAGGG TGTCCCATTC TTTCCTGTCT AAAACATTCA CTCTCCCCCG TCCTCACCTC

-467  TCCAGACAAG GAAGCTACAC AGGGTCTGGT ACAGTGAGAC AGTTCTGGTT TTCAGCAGGT GTAGGTGTGG GGCGGGGGAG GGGGGCCTTC ACCACACTCG

-367  ATGTCTTGTT TCTCATTCAC TAGGACTCCT AGAGGGTTGT GGGGGCGGGG TGGGGGTGGG AGGAAGACTG TCCAGATCTG AGCTGCTGAC CCCACAGGCA
                                                                                                            1/2 ERE
-267  GTGCCCTTGT GCCTGCCAGA ATCCAGGGCT CTGGGAATGT CCCTTCAGAT CCCCCGTTCC CCCACCCCCC TGCAGCCCTT CCTTTTGCTC AACCTTGCAC
                                                    NF-κB
-167  AGTTCCTGGG GGAGAGAGGG ACAGAAATCT TGCCAAGTAT TTCAACAGGA TGTGCTGGCA ATTACCTCAT GGCTTCCTGG ACTTGGTAAA GGATGGACTA
                                        NF-1                                    NF-κB      +1
-67   CCCCACCCTA CAAGGGGGGT TGGCAGCCAG GTAGGCCCAT AAAGAGGCCC CCTGAGGAGT CCTCCTCATT CTCTGCTCTT CCTCCTCCGG CACACATCGG
                                                        TATA BOX
 34   ACCTAGTAGC TGCTGAAACC ATGGGCCTGG GTGTCCTGTG TCTGGC
```

| BINDING SITE | CONSENSUS SEQUENCE | BINDING SITE | CONSENSUS SEQUENCE |
|---|---|---|---|
| TATA BOX | TATAAA | 1/2 ERE | $^A/_G$GGTCA |
| CAAT BOX | CCAAT | nGRE/nPRE(POMC) | |
| NF-1 | $T/_C GG^A/_C N_{5-6} GCCAA$ | nGRE/nPRE(PROLACTIN) | $AGGTCAN_{0-2}CGTCCA$ |
| NF-κB | | OCT-1, OCT-2 | ATCTCANNNTCATTA |
| CA REPEAT | $GGGA^A/_C TN^T/_C CC$ | | ATGCAAAT |
| | $(CA)_n$ | | |

FIG. 2B

```
-2910 AAGCTTGTGT GGTGGGACTA TGTAGAGCTG ACCCCCTCCC TGCAGCCCTG CTAGACTCTG AAGAGAGCCA AGGCCAGTGG GTAGGAGGAG ACAGGTCTGG
                                    ←
                                  1/2 ERE
-2810 AGCTGGTGCA GAGAGAGGAA TGAGCCCTGC ATGGGTTTGA TCAGAAACTC AGCCTTGTGT AGGGACACCC TGGGGCCCGG TGCTGTCCAT GCATGACCTC

-2710 ACAGAAGCGC AGAGCTGCCC TCTCTACAGA GGAGCGCCTG ATTTGTGTGG GAGCTAGGCA GAGATCTGCA TGCATGCGGA GGAGCCAGGC TTCAAGCCAG

-2610 CCTGGGGGAC CCCAAGCGGG ACTATCTCCC CTTCTGCACC TGGCTCTGGT GTCTTCCCAC TGTGGACCCA GTGCCCTGCT CACCCACCAC ATTCATACCC

-2510 TGGAGTCCTG GGTCCTCAGA GATCCATGAC ACTGCCTCAC CCCCAACTTC AAATTCTCTG GGGCTCCACC CGCTGGTCTC AGCTACGTGA AGCAGTCACC

-2410 GTAGACTAGA GGGTATTTTT TAGATTTAGG TCACTCTATC ATCCAGGCTG GAGTGCAGTG GCACAATCAT AGCTCACTGC AGCCTCGGCT TCCTGGGCCC
                                         1/2 ERE →
-2310 AAGTGATCCT CCCACCTCAG CCTCCCCGAG GATACGTGGT TTTTTTTTTC TTTTTTCAGA CAGGGTCTCA CTCTGTCTCC CAGGCTGGAG TGCAGTGGTG

-2210 CGATCTTGGC TCACTGCAGC CTCCGCCTCC CGGGTTCAAG CCATTCTCCT GCCTCAGCCT CCTGAGTAGT TGGGATCATA GGCATGCATC ACCCCACCTG

-2110 GCTAATTTTT GTATTTTTAG TAGAGACGGG GTTTTGCCAT ATTGGCCAGG CTAGTCCCTG AGGATCATTT TTTTTTCCCC GAGATGGAGT CTCCCTCTGT

-2010 CGCCCAGGCT GGAGTGCAAT GGCAACCTTG GCTCACTGCA ACCTCCGCCT CCCAGGTTCA AGCAATTCTT CTGCCTCAGC TTCCCGAGTA GTTGGGATTA

-1910 CAGGCATGCG CCACCATGCC CAACTAATCT TTGTATTTTT ACTAGAGACA GGGTTTCACC ATGTTGGTCA GGCTGGTCTT GAACACCTGA CCTCAGGTTA
                                                                                                    ←
                                                                                                  1/2 ERE
-1810 TCCACCCGCC TCAGTCTCCC AAAGTGCTGG AGTTACAGGC GAGAGCCACT GCGCCCAGCC GAGGATACCT TTTTTTTTTT TTTTAAGACA GAATATCGCT

-1710 CTGTTCCAGG CTAAAGTGCA AAGGCGTGAT CTCGGCTCAC TGCAACCTCC GCCTCCCAGG TTCAAGCTGT TCTTCTGCCT CAGCCTCCCG AGTAGCTGGG

-1610 ATTACAGGCG CCTGCCACCA TGCCCTGCTA ATTTTTGTAT TTTTAGTAGA GATGGGGTTT CACCGTGTTG GCCAGACTGG TCTCGAACTC CTGACCTCGT
                                                                                     1/2 ERE →      ← 1/2 ERE
-1510 GATCCACCCG CCTCAGCCTC CCAAATGCTG GGATTACAGA TGTGAGCCAC CGCACCCGGC CTGGCAGAGG ATACTTTTTA AGGTCAAAGA CAGTAGCAGA
                                                                                                 nPRE/nGRE
```

FROM FIG. 3A

```
-1410 GGTGGAGTTC CTGGGAACAG GGTCATGAGG GGAAGAGGGG GTTCGGAGGG AGCGAGTAGC CACTGGCTAC CTCTAGAAAG GGAAGGCTTT GGTGCAACAT
                             1/2 ERE →
-1310 CGTTCCCCTG CAGTTTTACT CATCTTTGCT TCCTGCCCTT TCATCATCCA ATCGGGCAGG CAGGACAGGG CCTGAGGGGG CAGGGATCCA GTGGGTGCCT
                                                                              CAAT BOX →
-1210 CTCTAGACTA ACCCCAGCTC AGGACTCCCA GAGCCCCTTC CCTGAGGCCC TGCTGCCCCC AAGCCCAGAT TGGGGATCCC AAGCAGCACG TAGGCAGAGC
                                                                                1/2 ERE →   CAAT BOX
-1110 CAGTGAGGTC CCCGTTAGTC CCATTGAAAG CTCTAAAACC AGCGAACCCT CAGTCCAGCC TCAGGTCAGG CATCCAGGAC GCCCTCAGCC TCATGGGTGA
                                                                            nGRE/nPRE (POMC)
-1010 GCCATCTCTG CGGACACTGC ACAGGGCCTA CGATCCATCG CTGCCTCCCG AGGATGCCAG CCAGGCCCCC GTTGAGATAA CTGCTTCCCT GCTGGACAAG

-910 GCTGGGACCA GCCATCTCGG TGACAGTTCC AGAACCCCTG GCCTGGGCTG CTGGGTTCAA TGGAAAAAGG CTGTGACTAG AGTCAGGGGG ATGGTCTCAG

-810 TGACCTCAAG GATAAGGCCA GATCCTTGCA CTGTCAGTGA CCCAAAGCAA CAGGTGTCCA GAGCAGCAGT GTGGCGCCTT CACGCCCCCA CACATCAGCC
          ← 1/2 ERE                       ← 1/2 ERE
-710 CAACTCACCC AGGACAGGGA CTGTAGCCTC AGCACTCAAC CCATGTGCCC TGTGTGGGGT CTCTTCCCAC TGCACTCACA GGAGAGGAAG GGTCCCTCAG

-610 GGGTCCACTG GGGTCCCCTC CTGCAAATGG GGCAAGGAGA GGGGCAAGGG GCTGTCTCAA GGCCCCTGGA GCACATGCAG GTCCTGGACT GGGGCTCCTG
                           OCTAMER
-510 GGAGGGCCAT GATTCTGGGC TCCATGAGTT CAGAGCAGAC GCCTTGTTTT TCCTTGTCCA CTGTCAGCCA CCCCACCCTT CCCTGACCCT TAAAAGAACC
                                                                                                       ← 1/2 ERE
-410 AGGAAACAGC ACATGATCTG TTGGAAGGAG GCATTCATTC TTTCCTTTCT GTGGGTGTGG GGAGGGACCA CAGGGCACAT ACCCCACCCT GGGATCCAGC

-310 TGAGCAGGGG GGTCAGAGAT GACAGCTCTT CCGGCTCACA GGCCACCGGC CCACATACAG GGCAATCAGA AGAAAGAAAC AGCACAAGGA AGGCACAGAG

-210 GGAGTCGTTG TCCCTGCCAG AGGTGCAGCA CTCCGGGAAT GTCCCTCACT CTCCCCGTCC CTCTGTCTTG CCCAATCCTG ACCAGGTGCA GAAATCTTGC
                                                    NF-κB →                        CAAT BOX →               NFI
-110 CAAGTGTTTC CGCAGGAGTT GCTGGCAATT GCCTCACATT CCTGGCCTTG GCAAAGAATG AATCAACCCA CCCTAGATCC CATAAATAGG GCCACCCAGG
     →         +1       NF-κB →                                                                TATA BOX
 -10 TGAGCCTCTC ACTCGCCACC TCCTCTTCCA CCCCTGCCAG GCCCAGCAGC CACCACAGCG CCTGCTTCCT CGGCCCTGAA ATCATGCCCC TAGGTCTCCT

91 GTGGCTGGGC CTAGCCCTGT TGGGGCTCTG CATGC
```

| BINDING SITE | CONSENSUS SEQUENCE | BINDING SITE | CONSENSUS SEQUENCE |
|---|---|---|---|
| TATA BOX | TATAAA | 1/2 ERE | $^A/_G$GGTCA |
| CAAT BOX | CCAAT | nGRE/nPRE(POMC) | |
| NF-1 | $^T/_C$GG$^A/_C$N$_{5-6}$GCCAA | nGRE/nPRE(PROLACTIN) | AGGTCAN$_{0-2}$CGTCCA |
| NF-κB | GGGA$^A/_C$TN$^T/_C$CC | OCT-1, OCT-2 | ATCTCANNNTCATTA ATGCAAAT |

FIG. 3B

```
RAT NRL    -2035 AGCTCCTCTGAGATTCTGGTCTCTGTTTTTCCTGACTAAAAATTCTTGGGGGCTCTGTCTACACCCAATAATCACCAGAGACTCAAGGGTGCCTTTGATT
                  II I      III I    I I   II II III II  II I  I III I IIII II  I     II  I     IIII I
HUMAN NGAL -2010 CGCCCAGGCTGGAGTGCAATGGCAACCTTGGCTCACTGCAA..CCTCCGCCTCCCAGGTTCAAGCAATTCTTCTGCCTCAGCTTCCCGAGTAGTTGGGAT

-1935 TATACATGAGTTTGTTTGTTTTAAGTCAAAGGCCTTGAGTGTATCCTTTGGCTTGCTTGCCTCAAACTCCCAATGCAGACCAGGCTCATCTGGCCTTGAA
                  II I    I     I  I III   I IIII    II IIII II  I    I III I I II III III
           -1912 TACAGGCATGCGCCACCATGCCCA.ACTAATCTTTGTATTTTTACTAGAGACAGGGTTTCACCATGTTGGTCAGGCTGGTCTTGAACACCTGACCTCAGG

-1835 GTCACAGAGATCCTTTGCCTCTGCACAGAGTGTTGGGCTTAAAGGTGGGAGCCACCACATACAGCTTTCAAGGAGACCTTT.................
                   I I    III I II    I II IIII III   III III I IIIIIII  I    IIII   I IIII IIIIII
           -1813 TTATCCACCCGCCTCAGTCT...CCCAAAGTGCTGGAGTTACAGGCGAGAGCCACTGCGCCCAGC...CGAGGATACCTTTTTTTTTTTTTTTAAGACAG

..................................................................................................

-1719 AATATCGCTCTGTTCCAGGCTAAAGTGCAAAGGCGTGATCTCGGCTCACTGCAACCTCCGCCTCCCAGGTTCAAGCTGTTCTTCTGCCTCAGCCTCCCGA

-1754 ............................................................CAAGCTAACGTGTTTAGTTGGAAGGT.TGGTTCTTT
                                                                             I IIIIIII    I   III I I  II
           -1619 GTAGCTGGGATTACAGGCGCCTGCCACCATGCCCTGCTAATTTTTGTATTTTTAGTAGAGATGGGGTTTCACCGTGTTGGCCAGACTGGTCTCGAACTCC

-1719 GTACTGTTGGAAATAGAATTTGGGGCCTCCCACGTGCTAGACAAACCCTCCACCATGGAGCTCTATTCCTCAGTTCTTGGATACCTTTTAAGGTCACAGA
                  II    II  I      IIIIIIIII IIII I I I      I III     I I    IIIIII IIIIIIIIIII III
           -1519 TGACCTCGTGATCCACCCGCCTCAGCCTCCCAAATGCT.GGGATTACAGATGTGAGCCACCGCACCCGGCCTGGCAGAGGATACTTTTTAAGGTCAAAGA

-1619 GGGTAGAAGGGGTGGATCCCCTAGG..........TCTGAGCTACAAGGGGCTGGAAGGGTGGGAGGTCCC...TGGTACCTCAAGAGTGACAGGCTCTG
                 IIII II IIIIII   III II              I  I  II IIII I I IIII IIIII   II    I IIIIII III  I I I    I
           -1420 CAGTAGCAGAGGTGGAGTTCCTGGGAACAGGGTCATGAGGGGAAGAGGGGGTTCGGAGGGAGCGAGTAGCCACTGGCTACCTCTAGAAAGGGAAGGCTTT

-1532 GTGGCCACATTGT..CCCCACAGCTTGGCTCAGCTTCACTTCCTGTCCTTTCATCATCCAGGGACCTGAGGGGACAGATTGTAGCGCTGTAGTCTTTCTG
                 I II IIIII II   III   III II  IIII III   IIIIIIII  IIIIIIIIIIIIIIIII                        II  I I
           -1320 GGTGCAACATCGTTCCCCTGCAGTTTTACTCATCTTTGCTTCCTGCCCTTTCATCATCCA..............................ATCGGGCAG
```

FROM FIG. 4A

```
-1434 ACATGGGAGAGGGGGAAGGCTGCATCCTAGGTGTGGGGGGATGTGAGGCTATAGCCTACTTATCAGGTTAAAATCCCCCTCTAAGCTTTCCCTCCTGGCT
         ||| ||| |||| |      ||| |       || |||  ||  || |  |  |||| || |   || |  ||
-1251 GCAGGACAGGGCCTGAGGGGGCAGGGATCCAGTGGGTGCCTCTCTAGACTAACCCCAGCTCAGGACTCCCAGAGCCCCTTCCCTGAGGCCCTGC..TGCC

-1334 AACCACCCTGAGCTAAGCAGCAGTGGAAGGGGGAGGTCAGGAGCAGCAAACAGATCAATAAGCCTTTTTAGTCCTGTGCAGGGCCAGAGGACTTCAGTCC
         | ||    ||| |     |||  | |||| |||  |     | || ||  ||| || |        |   |  |||||||
-1153 CCCAAGCCCAGATTGGGGATCCCAAGCAGCACGTAGGCAGAGCCAGTGAGGTCCCCGTTAGTCCCATTGAAAGCTCTAAAACCAGCGA.ACCCTCAGTCC

-1234 AGCCTTAGGTCAGATGTTCAGATGCGGATTCTGAGGAAGCCACCTGGCGGGGAGGGAAGCACAATATAGCATCTGGGATCCATCCATCGCAACCTTTCAA
      ||||| ||||||||  | ||| ||  ||| |          ||      |    |||  ||  || |||||||| |      |||
-1054 AGCCTCAGGTCAGGCATCCAG.GACGCCCTCAGCCTCATGGGTGAGCCATCTCTCCGGACACTGCACAGGGCCTACGATCCATCGCT.....GCCTCCCG

-1134 TGAATGTTAGCCAGGCCCCAGAGAGGAAAGGGCTTTTTTTTCAGCCCTAGGCTGGAATCAGC.........TGGGGAGAGAAAGTCCTAAGGCTGGGGCA
         | |||| |||||||||||| |   ||     |  ||  |  | ||||||| | ||||          |    || ||  | |||||
-960  AGGATGCCAGCCAGGCCCCCGTTGAGATAACTGCTTCCCTGCTGGACAAGGCTGGGACCAGCCATCTCGGTGACAGTTCCAGAACCCCTGGCCTGGGCTG

-1043 CTAAGTTCTCCTGCTCAAGGCTATGGCCAGAGACAGGGGGATGCCTTTTCTTTTCTTTTCTTTTTTCTTTTTTTTTTTTTTTTTTTTTTTTTTTGGTTCTGT
      || ||||   |  ||||||| || | |||| |||||||||||   |
-860  CTGGGTTCAATGGAAAAAGGCTGTGACTAGAGTCAGGGGGATGGTCTCAG.................................................

-943  TTTTCGGAGCTGGGGACCAAACCCAGGGGATGCCTTTTCAAGGGAGGATAACTTAAGGAGAAGGTG.GAACCTTGCTTCTGT.......CCAAAGTAACT
                                                          | || |||||| ||||   || |||||| ||||       |||||| |||
-810  .........................................................TGACCTCAAGGATAAGGCCAGATCCTTGC.ACTGTCAGTGACCCAAAGCAACA

-851  GGAGTACACTGGGCAGTTTGGACACACACACACACACACACACACACACACACACACCCCTACTTTTCCCAAGGGGCTGGTGCTCCCCCTTATCCTACGA
      || || ||                                                                         || || |||  | ||||    |  |
-758  GGTGTCCAG..........................................................................AGCAGC.AGTGTGGCGCCTTCACGCCCCC

-751  TGACAACAAGGTTGCAAGTCCTTGCCTTTGAAAGTGGCTGTATTCTAAGGACCGTGTGG..........................CACAGGAGAGGGG
         ||| ||   |  | ||  || ||| ||  |   |    || ||||                                       |||||||||||
-721  ACACATCAGCCCAACTCACCCAGGACAGGGACTGTAGCCTCAGCACTCAACCCATGTGCCCTGTGTGGGGTCTCTTCCCACTGCACTCACAGGAGAGGAA
```

FROM FIG. 4B

```
-679 TTGTCCCTGAGAGTTCAACTGCTGCCCTGTCTGCTCCTGTAAATGTCAGCATGGTCATGGGAAAGCAAAGGGGCTCAAGGGATTGGGCACCTCCAGGCTA
     ||||||| || | || ||||    ||| |||||| |||||         ||| ||| | |||||| ||||| ||    ||| ||||
-621 GGGTCCCTCAGGGGTCCACTG.....GGGTCCCCTCCTGCAAATG............GGGCAAGGAGAGGGGC...AAGGGGCTGT....CTCAAGGC...

-579 ATCTTCTGGCTGCCTCACCCTGTGCCAGGACCAAGTCCAAGCTTGACAGG....................CTTGGAACAGGGTGTCCCATTCTTTCCT
     ||||    ||| || || || |||| ||  | || |||                              || |  | ||  || ||| |
-552 ...CCCTGGAG..CACATGCAGGTCCTGGACTGGGGC...TCCTGGGAGGGCCATGATTCTGGGCTCCATGAGTTCAGAGCAGACGCCTTGTTTTTCCTT

-501 GTCTAAAA.CATTCACTCTCCCCCGTCCTCACCTCTCCAG..ACAAGGAAGCTACACAGGGTCTGGTACAGTGAGACAGTTCTGGTTTTCAGCAGGTGTA
     ||| |    || ||| |  |||   ||| ||| |   |   ||  ||||| | |||||| | ||| | ||||| | | ||| || | ||| |     |||
-455 GTCCACTGTCAGCCACCCCACCCTTCCCTGACCCTTAAAAGAACCAGGAAACAGCACATGATCTGTTGGAAGGAGGCATTCATTCTTTCCTTTC..TGTG

-404 GGTGTGGGGCGGGGG.AGGGGGGCC..TTCACCACACTCG........ATGTCTTGTTTCTCATTCACTAGGACTCCTAGAGGGTTGTGGGGGCGGGGTGG
     |||||||||| |||   |  |  |   |   |  |  |||        | |   |||   |   | |  ||   |||   |  ||    | |   | ||
-357 GGTGTGGGGAGGGACCACAGGGCACATACCCCACCCTGGGATCCAGCTGAGCAGGGGGGTCAGAGATGACAGCTCTTCCGGCTCACAGGCCACCGGCCCA

-314 GGGTGGGAGGAA.GACTGTCCAGATCTGAGCTGCTGACCCCACAGGCAGTGCCCTTGTGCCTGCCAGA.ATCCAGGGCTCTGGGAATGTCCCTTCAGATC
      | || |  |    |  |    | |||||  ||| | ||| ||||||||| |||  ||| ||  |   |||| ||||||||||||||| |
-257 CATACAGGGCAATCAGAAGAAAGAAACAGCACAAGGAAGGCACAGAGGGAGTCGTTGTCCCTGCCAGAGGTGCAGCACTCCGGGAATGTCCCTCACTCTC

-216 CCCCGTTCCCCCACCCCCCTGCAGCCCTTCCTTTTGCTCAACCTTGCACAGTTCCTGGGGGAGAGAGGGACAGAAATCTTGCCAAGTATTTCAACAGGAT
     ||                  | ||||    | |||| ||||| || |                      |||  ||||||||||||||||| ||||| |||||
-157 CC................CGTCCCTCTGTCTTGCCCAATCCTGACC...............AGGTGCAGAAATCTTGCCAAGTGTTTCCGCAGGAG

-116 GTGCTGGCAATTACCTCATGGCTTCCTGGACTTGGTAAAGGATGGACTACCCCACCCTACAAGGGGGGTTGGCAGCCAGGTAGGCCCATAAAGAGGCCCC
     ||||||||||| ||||     ||||||| |||||  |||| ||| |    |  ||||||||| |                  |||||||| ||| ||
-92  TTGCTGGCAATTGCCTCACA..TTCCTGGCCTTGGCAAAGAATGAATCAACCCACCCTAGAT.....................CCCATAAATAGGGCCA

-16  CTGAGGAGTCCTCCTCATTCT....CTGCTCTTCCTCCTCCGG................CACACATCGGACCTAGTAGCTGCTGAAACCATGGGCCTGGG
     | ||| | |||| ||  || ||||||| || |  ||||  | | || |  |||||| |||| ||| ||
-16  CCCAGGTGAGCCTCTCACTCGCCACCTCCTCTTCCACCCCTGCCAGGCCCAGCAGCCACCACAGCGCCTGCTTCCTCGGCCCTGAAATCATGCCCCTAGG

65  TGTCCTGTGTCTGG
     | ||||||||||||
 85  TCTCCTGTGGCTGG
```

FIG. 4C

MAMMARY GLAND-SPECIFIC PROMOTERS

This invention was made with United States government support awarded by NIH Grant #: CA 58328. The United States Government has certain rights in this invention.

FIELD OF THE INVENTION

In general, the field of the invention is mammary gland-specific promoters. Specifically, the field of the present invention is mammary gland-specific promoters isolated from the rat NRL gene and the hum an NGAL gene.

BACKGROUND

The oncogene c-erbB-2 is known to be associated with the clinical progression of human breast cancer. In vivo models utilizing c-erbB-2's rodent homolog, neu, have been developed to try to evaluate the role of c-erbB-2 in mammary carcinogenesis and tumor biology. In one model, transgenic mice have been generated in which the expression of activated neu is targeted to the mammary gland using mammary-specific promoters. In a second model the activated neu oncogene has been directly and stably introduced into in situ rat mammary epithelial cells, using a replication-defective retroviral vector. With both methods, neu was found to be a potent tumor inducer.

The isolation of a lipocalin uniquely overexpressed in neu-initiated rat mammary carcinomas has been reported in S. Stoesz, et al., 1994 AACR Abstract. This lipocalin has been named "NRL" for neu-related lipocalin. (The disclosure of this abstract and of all other publications referred to herein are incorporated by reference as if fully set forth herein.) As lipocalins are known to have a wide range of functions, the specific function of NRL is not known.

A protein somewhat homologous to rat NRL, human NGAL, has been isolated and sequenced. Various cDNA gene sequences coding for NGAL and the NGAL protein sequence have been reported in L. Kjeldsen, et al., *J. Biol. Chem.* 268:10425–10432 (1993); J. Bundgaard, et al., *Biochem. Biophys. Res. Comm.* 202 [3]:1468–1475 (1994); S. Bartsch, et al., *FEBS Let.* 37:255–289 (1995). NGAL (also known as neutrophil lipocalin/HNL) has been found in a variety of cell types (e.g. bone marrow; ovarian cell cancers). Again, the specific function of NGAL is not known.

Note that Bundgaard, et al. reported the first base of the mature protein as Q from CAG, whereas Kjeldsen, et al. at one location reported an E at that position. The present claims use "NGAL" to cover both variants.

SUMMARY OF THE INVENTION

In one embodiment, the present invention is an isolated DNA fragment comprising a mammary gland-specific promoter that promotes gene expression throughout the reproductive cycle. In a preferred embodiment of the invention, the promoter promotes gene expression in a constant manner throughout the estrous cycle. The promoter also promotes gene expression throughout the pregnancy, lactation and involution stages in a non-constant manner. The promoter is capable of strongest gene promotion in the involution stage and the weakest gene promotion in the pregnancy stage.

In one particularly advantageous form of the invention, the promoter is the rat NRL promoter or the human NGAL promoter. However, promoters to homologs of the NRL and NGAL genes found in other species are also envisioned to be suitable for the present invention. For example, an NGAL homolog has been isolated from mouse (24P3 oncoprotein).

In one embodiment, the mammary gland-specific promoter comprises nucleotides 1 through 2967 of SEQ ID NO:1. Preferably, the promoter comprises nucleotide sequences 1154 through 2967 of SEQ ID NO:1. In another embodiment of the present invention, the promoter comprises sequences 1 through 2910 of SEQ ID NO:2. Preferably, the promoter comprises nucleotides 1102 through 2910 of SEQ ID NO:2.

In another embodiment of the invention, the promoter consists of fragments of SEQ ID NOs:1 and 2 that have been truncated at the 5'-end. These truncated fragments will still possess the same mammary-specific gene expression properties as full-length SEQ ID NOs:1 and 2.

In another embodiment of the present invention, the promoter is part of a vector molecule, such as a plasmid or virus vector. In an especially preferred embodiment, the vector molecule comprises a mammary gland-specific promoter operably connected to a gene sequence. This embodiment of the present invention may be used to create a transgenic animal with gene expression targeted to the mammary gland in a developmental manner consistent with the expression of the rat NRL and human NGAL genes.

In another embodiment, the present invention is a transgenic non-human mammal comprising the vector described above.

It is an object of the present invention to provide a mammary gland-specific promoter with distinctive developmental regulation.

It is another object of the present invention to provide a mammary gland promoter with constant expression throughout the estrous cycle.

It is another object of the present invention to provide a transgenic mammal containing the promoter of the present invention operably connected to a foreign gene.

It is another object of the present invention to provide a mammary-specific promoter as a drug target for breast cancers.

Other objects, features and advantages of the present invention will become apparent after examination of the specification, drawings and claims.

DESCRIPTION OF THE DRAWINGS

FIG. 1 is a sequence comparison of cDNAs of hPGDS2, rPGDS2, rNRL and hNGAL.

FIG. 2 is a sequence analysis of rat NRL promoter (SEQ ID NO:1).

FIG. 3 is a sequence analysis of human NGAL promoter (SEQ ID NO:2).

FIG. 4 is a sequence comparison between rat NRL and human NGAL promoters.

DESCRIPTION OF THE INVENTION

In one embodiment, the present invention is an isolated DNA fragment comprising a mammary gland-specific promoter capable of promoting gene expression throughout the mammalian reproductive cycle. The promoter is most conveniently isolated from the 5' region of either the rat NRL gene or the human NGAL gene. The Examples below demonstrate one particularly advantageous method of isolating the promoter.

The mouse mammary tumor virus (MMTV) promoter (Truss, et al., *J. Steroid Biochem. Molec. Biol.* 43[5]

365–378,1992) and the whey acidic protein (WAP) gene promoter (Li and Rosen, Molecular Endrochrinology, 8[10]:1328–1334, 1994) are two examples of mammary-specific promoters with developmental expression patterns that differ from the promoters of the present invention.

In the method described below, specific PCR promoters were developed from a comparison of the rat NRL cDNA, the human NGAL cDNA and the rat and human brain prostaglandin D2 synthase cDNA 'see FIG. 1). FIG. 1 is a sequence comparison of cDNAs of hPGDS2, rPGDS2, rNRL and hNGAL (SEQ ID NOs:3, 4, 5 and 6). The inverted triangles indicate the splicing sites that have been characterized for human prostaglandin $D_2$ synthase gene. Primers rNRL-A2, hNGAL-A2, rNRL-R3 and hNGAL-R2 (SEQ ID NOs:7, 8, 9 and 10) were useful in amplifying these 5' regions.

This amplification was by standard PCR reaction. In this manner, a set of genomic clones were isolated corresponding to the rat NRL gene and the human NGAL gene.

If one of skill in the art is interested in isolating promoters from other NGAL homologs, such as mouse, an analogous procedure may be followed.

The mouse NGAL (24p3) was initially isolated in a search for genes overexpressed during a SV40-induced mitotic reaction (*Oncogene* 4(g):601–608, 1989). The gene encodes the mouse 24p3 and promoter region (793 bp) has recently been isolated (*Gene* 170(2):173–180, 1996).

One may test these candidate promoters by the experiments described below the Examples. A successful mammary gland-specific promoter will promote gene expression in a constant manner throughout the estrous cycle.

These clones were analyzed and screened for the first exon-containing clones by a standard PCR method using a first exon forward primer and a second exon reverse primer of the NRL NGAL genes, respectively.

SEQ ID NOs:1 and 2 (FIGS. 2 and 3) are the result of sequence analysis of the rat NRL 5' region and the human NGAL 5' region, respectively. FIG. 2 is a sequence analysis of rat NRL promoter (SEQ ID NO:1). "+1" indicates the putative transcription start site. The promoter and upstream region is indicated in negative number relative to the transcription start site. Putative response elements are also indicated. FIG. 3 is a sequence analysis of human NGAL promoter (SEQ ID NO:2). "+1" indicates the putative transcription start site.

The promoter and upstream region is indicated by a negative number relative to the transcription start site. Putative response elements are also indicated.

Another way to obtain the same promoter sequences would be to use primers derived from SEQ ID NOs:1 and 2 to directly amplify the sequences found in SEQ ID NOs:1 and 2 from rat or human genomic DNA.

It is well known by those of skill in molecular biology that the entire 5' region of a gene is not needed to confer specific developmental regulation properties. We analyzed the sequences in SEQ ID NOs:1 and 2 to determine what regions would be strictly necessary for developmental regulation consistent with the natural regulation of the rat NRL or human NGAL gene. FIG. 4 is a sequence comparison between rat NRL and human NGAL promoters. Periods are introduced for best alignment between NRL and NGAL. Vertical bars indicate the bases identical between NRL and NGAL. The regions with long stretch of homology are high-lighted with vertical bars. Tables 1 and 2 in the Examples below detail the placement of the TATA box and putative ERE and PRE/GRE half-sites. Because the two promoters demonstrate homology up to base −1810, we envision that at least 1810 nucleotides of each 5' region are needed for sufficient developmental regulation. However, we envision that further truncations from the 5'-end of the promoter will also result in promoter fragments with equivalent abilities to promote mammary-specific gene expression. These promoters are also envisioned to be suitable for the present invention.

Additionally, we envision that the nucleotide region between 1154 and 2967 of SEQ ID NO:1 and 1102 and 2910 of SEQ ID NO:2 are preferred promoters of the present invention.

In one embodiment, the present invention is a promoter that provides developmental expression of a gene consistent with the natural expression of the rat NRL and human NGAL genes. We have studied the expression of these RNAs in different stages of the mammalian reproductive cycle, including estrous, pregnancy, lactation and involution stages. The expression of both RNAs is relatively constant throughout the stages of the estrous cycle (diestrous, proestrous and estrous). By "constant" we mean that the expression does not change by more than 10% throughout the estrous cycle.

The mRNAs are also expressed throughout pregnancy and lactation and involution. In both systems, the mRNA is expressed most strongly in involution and most weakly in pregnancy. As the examples below demonstrate, expression varies between .5 fold in the pregnant mammary gland to 4 fold during involution.

In another embodiment, the present invention is the isolated promoter fragment combined in a vector, most preferably operably connected to a foreign gene sequence. Preferable examples of vectors include both plasmid and viral vectors.

In this manner, foreign gene expression can be targeted to a mammary gland. For example, one may want to target the expression of a therapeutic molecule to the estrous cycle. It is an advantage in many applications that the expression is fairly level or constant throughout the various stages of reproduction.

Another embodiment of the present invention is the use of the mammary-specific promoters as a drug target for breast cancer genes. As described above, these genes are overexpressed in a subset of breast cancers and the up-stream regions of these genes are likely therapeutic targets.

EXAMPLES mRNA Expression

Human diseases or cancers are usually studied using animal models in order to obtain important information that may one day be applied to human therapy. Of the known oncogenes, c-erbB2 is most commonly associated with the clinical progression of human breast cancer. Activated neu oncogene (neu*), the rodent equivalent of c-erbB2, is extremely potent in inducing mammary carcinoma in rats. To explore the mechanism of neu*-initiated mammary carcinogenesis, a subtraction hybridization-based method was used to isolate cDNA clones derived from mRNAs that were differentially expressed in neu*-induced tumors versus normal mammary glands. One cDNA clone was isolated and designated as neu-related lipocalin NRL (Stoesz and Gould, supra, 1995). Northern analysis using NRL cDNA probe revealed that NRL mRNA levels in neu*-induced tumors is 12-fold of that in normal mammary glands. This enhanced expression is specific to activated neu-induced tumors and is not observed in tumors induced either by activated-ras, chemical carcinogens DMBA, or NMU. Sequence analysis revealed that rat NRL is highly homologous to the human neutrophil gelatinase associated lipocalin (NGAL) and mouse oncogenic lipocalin-24P3.

A tissue distribution study revealed that expression of NRL mRNA was largely confined to the mammary gland (Stoesz and Gould, supra, 1995). No mRNA expression was observed in rat liver, spleen, muscle, kidney or brain. The expression of NRL in the mammary gland under different physiological conditions was evaluated by Northern blot analysis. Expression of the NRL mRNA did not vary significantly throughout the estrous cycle, but varied significantly during pregnancy (day 18), lactation (day 4) and involution (day 6). The mRNA levels decreased in the pregnant mammary gland (0.5-fold expression compared to virgin mammary gland), then increased during the lactation (1.5-fold) and involution (>4-fold).

The expression of the gene only in mammary gland and steady mRNA levels during estrous cycle suggest that the NRL gene has a mammary gland-specific promoter than is not significantly regulated by estrous hormones. The increased mRNA levels of NRL during involution suggests that NRL expression may be directly or indirectly regulated by estrogen. A preliminary study with a human specimen revealed that the NGAL (human homologue of NRL) expression levels were inversely correlated with estrogen receptor levels.

In the Examples below, we describe the cloning, sequencing and sequence analyses of promoters and upstream regions of the rat NRL and human NGAL genes.

Genomic Clone Isolation

There are several different ways to isolate a promoter sequence. One approach is to screen a genomic library using a cDNA probe corresponding to the gene studied. This approach is fairly labor-intensive and does not always generate clones containing the promoter and up-stream transcriptional regulatory sequences. The second approach is to amplify the promoter-containing fragment directly from genomic DNA by a PCR-based method. This approach requires cDNA sequence of the very first exon of the gene studied and each run only generates a few hundred bases new sequence. Several runs of extension may be necessary to cover a range of few thousand base pairs and mis-incorporation of nucleotide could be introduced by PCR during the repeated process.

The third approach, which we took, is to PCR-amplify genomic fragments using oligonucleotide primers derived from rat NRL and human NGAL cDNA sequences. From the sequences of genomic fragments, we generate genomic specific oligonucleotide primers and use them to isolate P1 plasmid clones by PCR screening. The average insert size of a P1 clone is about 80 to 100 kb, which is large enough to cover an entire gene of average size. The P1 clone can serve not only as a source of promoter sequence but also a good probe for chromosomal localization by fluorescence in situ hybridization.

Gene structure of either the rat NRL or the human NGAL is not known. It has been observed that genes within the same family, especially within the same subfamily, usually share a common gene structure. Therefore, we compared the cDNA sequences of rat NRL and human NGAL to the rat and human brain prostaglandin $D_2$ synthetase cDNAs that also belong to the lipocalin family with known intron-exon boundaries. Although a relatively small transcript, the human brain prostaglandin $D_2$ synthetase gene contains 7 exons (White, et al. *J. Biol. Chem.* 267(32):23202–23208, 1992). The sequences spanning the intron-exon boundaries are well conserved among rat PGDS2, human PGDS2, rat NRA and human NGAL cDNAs (FIG. 1, SEQ ID NOs: 3, 4, 5 and 6). Several primer sets were prepared and tested for PCR-amplification of NRL from rat spleen DNA and NGAL from human DNA (MCF-7 cells).

Genomic fragments of rat NRL and human NGAL were amplified by PCR with primers derived from the second and the third exons. Partial sequencing of the amplified NRL and NGAL DNA revealed the intron-exon boundaries at exactly the position predicted from FIG. 1. In combination with forward primers (rNRL-A2 and hNGAL-A2, SEQ ID NOs:7 and 8) of the second exon, reverse primers (rNRL-R3 and hNGAL-R2, SEQ ID NOs:9 and 10) derived from the second intron were tested for PCR amplification. Genomic fragments of predicted sizes were amplified and sequences determined. These characterized rat NRL primer set (rNRL-A2 and rNRL-R3) and human NGAL set (hNGAL-A2 and hNGAL-R2) were sent to Genome Systems St. Louis, Mo., to isolate the corresponding P1 clones by a PCR-based method.

In this manner, three independent P1 plasmid clones were isolated for rat NRL and three for human NGAL. Host cells harboring the P1 plasmid were further verified by PCR using rNRL and hHNGAL primer sets that differ from those used for screening. The verified P1 clones were then purified by re-plating the cells at low density and examined by PCR. P1 plasmid preparations of purified clones were digested with either endonucleases EcoRI or HindIII and subjected to Southern blot analysis with DNA probe containing the first exon. The rat NRL probe detected a 8-kb EcoRI band and a 3-kb HindIII band of NRL P1 plasmid respectively. The human hNGAL probe only hybridized to bands of relatively high molecular weight (>7 kb) in either digestion. Aliquots of the same digestions used for Southern analysis were subcloned into modified pSP73 plasmid vector (with a NotI site introduced at SmaI site).

The subclones were screened for first exon-containing clones by a PCR method using a first-exon forward primer and second-exon reverse primer of the NRL and NGAL genes, respectively. Plasmid DNAs of positive clones were mapped by restriction digestion and PCR amplification with various primer combinations of NRL, NGAL and vector primers. Selected positive clones were then sequenced upward from the end of the first exon and downward from the 5'-end. Both rat NRL and human NGAL sequences were analyzed for putative transcription regulatory elements.

FIG. 2 is a sequence 5' region of the region of the rat NRL gene. SEQ ID NO:1 repeats this sequence.

FIG. 3 is the sequence 5' region of the human NGAL gene. SEQ ID NO:2 repeat this sequence.

Analysis of the 5'-end of NRL and NGAL Genes

Table 1, below summarizes some of our analysis of the 5' up stream region of the NRL and NGAL genes. The "5' up-stream region" designated in the table extends from the beginning of the 5'-end of the sequenced region to the putative transcription initiation site. The TATA-box designation is relative to the putative transcription initiation at +1 in FIGS. 2 and 3 for the rat NRL gene and for the human NGAL gene. Referring to Table 1, the TATA box is where the general transcription machinery recognizes and binds. It has been observed that the NGAL levels are inversely correlated to the estrogen receptor (ER) and/or progesterone receptor (PR) levels in T47D cell (a human breast cancer cell line). ER or PR regulate their target gene expression through binding to those specific response elements (ERE or PRE) in the regulatory regions. Therefore, searching for putative estrogen receptor binding sites or progesterone receptor bind site will facilitate characterizing the role of ER or PR in NGAL expression. Negative GRE/PREs have been identified in bovine prolactin promoter (*Gene & Development* 2:1144–1154, 1988) and rat Pro-Opiomelanocortin promoter (Mol. Cell. Biol. 9(12), 1989). Negative ERE may contain sequence similar to that of positive ERE which consists of direct repeats of $^A/_G$GGTCA half-site.

TABLE 1

|  | Rat NRL genomic DNA | Human NGAL genomic DNA |
| --- | --- | --- |
| 5' upstream region | 2967 bp | 2910 bp |
| TATA-box | ATAAAGA at −29 | ATAAATA at −29 |
| putative ERE-half site | A/$_G$GGTCA, many | A/$_G$GGTCA, many |
| putative-(PRE/GRE) | TCYACNnnnTGATCW, many | TCYACNnnnTGATCW, many |

The rat NRL and human NGAL promoters are highly homologous to each other in the regions listed above. FIG. 4 is a sequence comparison between the rat NRL and the human NGAL promoters. No extended homology was identified between rat NRL and human NGAL beyond the base −1820. Response elements identified within the homologous regions include TATA box, nuclear factor 1(NF-1)-binding site, NF-κB-binding site, negative glucocorticoid/progesterone response element (nGRE/nPRE), and a half-site of estrogen response element (½ ERE). Additional elements yet to be identified are also presented in these homologous regions. These homologous regions likely harbor those transcription regulatory elements important to both rat NRL and human NGAL genes. Therefore, these regions may also be conserved in NRL/NGAL homologs of all other mammalian species as well.

TABLE 2

Regions with extended homology

| NRL promoter | NGAL promoter | Putative response elements |
| --- | --- | --- |
| −32 to +18 | −32 to +22 | TATA box |
| −151 to −56 | −127 to −34 | NF-1 binding site, NF-κB-binding site |
| −192 to −171 | −152 to −131 |  |
| −275 to −224 | −217 to −167 | NF-κB-binding site |
| −462 to −370 | −413 to −321 |  |
| −621 to −595 | −586 to −562 |  |
| −651 to −635 | −603 to −587 | Oct-1, Oct-2 binding site |
| −692 to −659 | −634 to −601 |  |
| −862 to −844 | −769 to −751 |  |
| −892 to −863 | −806 to −777 |  |
| −1027 to −1001 | −844 to −818 |  |
| −1088 to −1073 | −914 to −899 |  |
| −1133 to −1114 | −959 to −940 |  |
| −1243 to −1214 | −1063 to −1036 | nGRE/nPRE (POMC), ½ ERE |
| −1529 to −1475 | −1317 to −1261 |  |
| −1584 to −1564 | −1375 to −1355 |  |
| −1641 to −1604 | −1442 to −1405 | nGRE/nPRE (POMC/Prolactin), ½ ERE |
| −1695 to −1682 | −1495 to −1482 |  |
| −1810 to −1755 | −1791 to −1739 |  |

We did an extensive sequence comparison of the human NGAL and rat NRL promoters to those of other members of lipocalin superfamily with known gene structure, including mouse 24p3 (X81627, *Gene* 170(2):173–180, 1996), human prostaglandin D$_2$ synthase (M98537, *J. Biol. Chem.* 267(32):23202–23208, 1992), rat prostaglandin D synthase (M94134, *Proc. Natl. Acad. Sci. U.S.A.* 89(12):5376–5380, 1992), human tear prealbumin (TP) gene (L14927, *Gene* 139(2):177–183, 1994), rat epididylma secretory protein I (X59831, *Biochem. J.* 281(Pt 1):203–210, 1992), rat von Ebner's gland protein I (X74805) and II (X74807, *Eur. J. Biochem.* 211(3):905–916, 1994). Based on the comparison, we obtained a putative transcriptional start site for the rat NRL promotor and the human NGAL promotor.

In mouse NGAL (24p3), a putative glucocorticoid response element has been identified at −520 to −501. However, the two GRE half-sites are not well conserved in human and rat NGAL promoters. Transcriptional activity analysis of serial deleted 24p3 promoter reveals that the putative GRE plays only a minor role in response to glucocorticoid (dexamethasone, Dex). The major element responds to Dex is located between base −198 and −155 with no homology to any known transcription factor-binding site. This region is highly homologous between mouse and rat (base −208 to −165), but with low homology to human NGAL, suggesting that this element is rodent-specific. In summary, the characterization of mouse 24p3 promoter is still preliminary at this point.

Two putative NF-κB-binding sites have been identified in the proximal region of NGAL promoters of human, rat (Table 2) and mouse. The distal NF-κB-binding site (GGGAATGTCC, SEQ ID NO:14) is identical among human, rat and mouse (at −176, −235, −230, respectively). The proximal NF-κB-binding site is also conserved among these species with one or two bases variation.

| human | GGCAATTGCC | at −87 (SEQ ID NO: 11) |
| --- | --- | --- |
| rat | GGCAATTAAC | at −111 (SEQ ID NO: 12) |
| mouse | GGCAATTACT | at −109 (SEQ ID NO: 13) |

NF-κB has been implicated in the induction of several genes involved in the early process of immune and inflammatory responses. One of those gene involved is interleukin 6 (IL-6). Glucocorticoids are well known for their anti-inflammatory activity. Glucocorticoids strongly repress IL-6 gene expression through the direct interaction between glucocorticoid receptor and the p65 subunit of transcription factor NF-κB (*PNAS* 91(2):752–756, 1994). In addition, estrogen receptor has also been demonstrated to repress the IL-6 promoter through interaction with NF-κB (*Mol. Cell. Biol.* 15(9):4971–4779, 1995). Progesterone receptor and glucocorticoid receptor share the same DNA response element. The lower expression levels of NGAL in ER/PR positive T47D cells could be due to the repression of NGAL promoter by ER and/or PR directly or through interaction with NF-κB.

Only 793 base pairs upstream the transcription start site of mouse 24p3 has been reported. Homologous sequences beyond this region have been identified between human and rat NGAL promoters up to base −1810 (Table 2 and FIG. 4). Homologous sequences in this region (−790 to −1810) include several putative negative GRE/PRE and ERE half-sites. They could be important elements involved in the regulation of NGAL promoter activity.

GGGAATGTCC                                                                                          10 we claim:

1. An isolated DNA fragment comprising a promoter, wherein the promoter promotes gene expression in a constant manner throughout the estrous cycle and wherein the promoter is selected from the group consisting of neu-related lipocalin (NRL) or neutrophil gelatinase associated lipocalin (NGAL) promoters.

2. The isolated DNA fragment of claim 1, wherein the fragment comprises a promoter isolated from the rat NRL gene.

3. The isolated DNA fragment of claim 1 wherein the fragment comprises a promoter isolated from the NGAL gene.

4. The isolated DNA fragment of claim 3, wherein the fragment comprises the human NGAL promoter.

5. An isolated DNA fragment comprising a promoter, wherein the promoter promotes gene expression in a constant manner throughout the estrous cycle and wherein the promoter comprises nucleotides 1 through 2967 of SEQ ID NO:1.

6. An isolated DNA fragment comprising a promoter, wherein the promoter promotes gene expression in a constant manner throughout the estrous cycle and wherein the promoter comprises nucleotides 1154 through 2967 of SEQ ID NO:1.

7. An isolated DNA fragment comprising a promoter, wherein the promoter promotes gene expression in a constant manner throughout the estrous cycle and wherein the promoter comprises nucleotides 1 through 2910 of SEQ ID NO:2.

8. An isolated DNA fragment comprising a promoter, wherein the promoter promotes gene expression in a constant manner throughout the estrous cycle and wherein the promoter comprises nucleotides 1102 through 2910 of SEQ ID NO:2.

9. A vector comprising the promoter of claim 1.

10. A vector comprising the promoter of claim 2.

11. A vector comprising the promoter of claim 3.

12. The vector of claim 9 additionally comprising a gene sequence operably connected to the promoter.

13. The vector of claim 10 additionally comprising a gene sequence operably connected to the promoter.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 3046 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
GAATTCCGCA  AGCAGACCTG  AGGGCCAGGC  TGGAGAGTGG  AGCTGCGTTC  GCTCCAGCCC      60
CTCAAGGCCA  GGCTCACCAG  TTTCTGCAGT  GAGTTTCTGG  ATCAGAATGT  CAGACTGGAT     120
TCTTGAAATG  CAGTAACCTC  GGAGCCTCTC  ATGTGGAATG  GACCTAGGTC  GGGTTGTGTA     180
GCAGTTAGAG  TTCTTGGGCT  TTATGACCAC  AGAAAACTCA  AGTGTGACCT  AGATGTGTTA     240
CTACTAAGTT  CAGGGTCAGC  ACAGATTACA  CAATGAGACC  TCATATCAAA  ATAAATAATA     300
AATAATAAAA  AGAAGTAGCG  GGGGCTGGGG  ATTTAGCTCA  GTGGCAGAGC  GCTTACCTAG     360
GAAGCGCAAG  GCCCTGGGTT  CGGTCCCCAG  CTCCGAAAAA  AAAAGAAAA   AAAAAAAAA      420
AAAAAAAGAA  GTGGCTGGCT  TGGTTGGCGA  TGTGTGCCAA  CACTCAGAGG  TAGAATCAAG     480
AGAACAAGGG  AAGGAAGGAA  GAGGGAGGAA  GGAAGGGAAG  GAGGGAGGAA  GGAAGAAGAA     540
GGGAGGGAGG  GAAGAAGGAG  GTGGGAGGAA  GGAAGGAAAG  AAGGAAAGAG  ACCGACTGGA     600
CGAGAGGTGG  AGGCAGGGGG  ATGAGAAGTT  CAAAGTCATC  TTTGGTGACA  TAGGGAGTTT     660
GAGGCTACCT  GGCCTTTAGG  GATTCAGTTT  CAGAGAGAGA  GGGTTCATGG  GAGAGCTGGC     720
AGGATCCTGG  GGGAAGAATC  AGCAGGCTGA  AGGTGGCTGT  GTGCCTTGTA  CCTGGAACAG     780
CCAGGGTCCT  GAGCTAGGCC  ATCTCCCCTC  CCACCCTTAA  TTCTGACCTT  TTAGTTTTTC     840
CAGACCCAGC  TCTCTGCCCC  AGTTCATACT  GGCTCGGTTC  CACTGGTCAC  TCTGCCCCCT     900
GGTTTTCAGA  CTCTAGAATA  TCCTGCCTGT  CCAGCTCCTC  TGAGATTCTG  GTCTCTGTTT     960
TTCCTGACTA  AAAATTCTTG  GGGGCTCTGT  CTACACCCAA  TAATCACCAG  AGACTCAAGG    1020
GTGCCTTTGA  TTTATACATG  ACTTTCTTTC  TTTTAAGTCA  AAGGCCTTGA  GTGTATCCTT    1080
TGGCTTGCTT  GCCTCAAACT  CCCAATGCAG  ACCAGGCTCA  TCTGGCTTTG  AAGTCACAGA    1140
GATCCTTTGC  CTCTGCACAG  AGTGTTGGGC  TTAAAGGTGG  GAGCCACCAC  ATACAGCTTT    1200
CAAGGAGACC  TTTCAAGCTA  ACGTGTTTAG  TTGGAAGGTT  GGTTCTTTGT  ACTGTTGGAA    1260
ATAGAATTTG  GGGCCTCCCA  CGTGCTAGAC  AAACCCTCCA  CCATGGAGCT  CTATTCCTCA    1320
GTTCTTGGAT  ACCTTTTAAG  GTCACAGAGG  GTAGAAGGGG  TGGATCCCCT  AGGTCTGAGC    1380
TACAAGGGGC  TGGAAGGGTG  GGAGGTCCCT  GGTACCTCAA  GAGTGACAGG  CTCTGGTGGC    1440
CACATTGTCC  CCACAGCTTG  GCTCAGCTTC  ACTTCCTGTC  CTTTCATCAT  CCAGGGACCT    1500
GAGGGGACAG  ATTGTAGCGC  TGTAGTCTTT  CTGACATGGG  AGAGGGGAA   GGCTGCATCC    1560
TAGGTGTGGG  GGGATGTGAG  GCTATAGCCT  ACTTATCAGG  TTAAAATCCC  CCTCTAAGCT    1620
TTCCCTCCTG  GCTAACCACC  CTGAGCTAAG  CAGCAGTGGA  AGGGGAGGT   CAGGAGCAGC    1680
AAACAGATCA  ATAAGCCTTT  TTAGTCCTGT  GCAGGGCCAG  AGGACTTCAG  TCCAGCCTTA    1740
GGTCAGATGT  TCAGATGCGG  ATTCTGAGGA  AGCCACCTGG  CGGGAGGGA   AGCACAATAT    1800
```

| | | | | | | |
|---|---|---|---|---|---|---|
| AGCATCTGGG | ATCCATCCAT | CGCAACCTTT | CAATGAATGT | TAGCCAGGCC | CCAGAGAGGA | 1860 |
| AAGGGCTTTT | TTTTCAGCCC | TAGGCTGGAA | TCAGCTGGGG | AGAGAAAGTC | CTAAGGCTGG | 1920 |
| GGCACTAAGT | TCTCCTGCTC | AAGGCTATGG | CCAGAGACAG | GGGGATGCCT | TTTCTTTTCT | 1980 |
| TTTCTTTTTT | CTTTTTTTTT | TTTTTTTTTT | TTTTTGGTT | CTGTTTTTCG | GAGCTGGGGA | 2040 |
| CCAAACCCAG | GGGATGCCTT | TTCAAGGGAG | GATAACTTAA | GGAGAAGGTG | GAACCTTGCT | 2100 |
| TCTGTCCAAA | GTAACTGGAG | TACACTGGGC | AGTTTGGACA | CACACACACA | CACACACACA | 2160 |
| CACACACACA | CACCCCTACT | TTTCCCAAGG | GGCTGGTGCT | CCCCCTTATC | CTACGATGAC | 2220 |
| AACAAGGTTG | CAAGTCCTTG | CCTTTGAAAG | TGGCTGTATT | CTAAGGACCG | TGTGGCACAG | 2280 |
| GAGAGGGGTT | GTCCCTGAGA | GTTCAACTGC | TGCCCTGTCT | GCTCCTGTAA | ATGTCAGCAT | 2340 |
| GGTCATGGGA | AAGCAAAGGG | GCTCAAGGGA | TTGGGCACCT | CCAGGCTAAT | CTTCTCCCTC | 2400 |
| CCTCACCCTG | TGCCAGGACC | AAGTCCAAGC | TTGACAGGCT | TGGAACAGGG | TGTCCCATTC | 2460 |
| TTTCCTGTCT | AAAACATTCA | CTCTCCCCCG | TCCTCACCTC | TCCAGACAAG | GAAGCTACAC | 2520 |
| AGGGTCTGGT | ACAGTGAGAC | AGTTCTGGTT | TTCAGCAGGT | GTAGGTGTGG | GGCGGGGGAG | 2580 |
| GGGGGCCTTC | ACCACACTCG | ATGTCTTGTT | TCTCATTCAC | TAGGACTCCT | AGAGGGTTGT | 2640 |
| GGGGGCGGGG | TGGGGGTGGG | AGGAAGACTG | TCCAGATCTG | AGCTGCTGAC | CCCACAGGCA | 2700 |
| GTGCCCTTGT | GCCTGCCAGA | ATCCAGGGCT | CTGGGAATGT | CCCTTCAGAT | CCCCGTTCC | 2760 |
| CCCACCCCCC | TGCAGCCCTT | CCTTTTGCTC | AACCTTGCAC | AGTTCCTGGG | GGAGAGAGGG | 2820 |
| ACAGAAATCT | TGCCAAGTAT | TTCAACAGGA | TGTGCTGGCA | ATTACCTCAT | GGCTTCCTGG | 2880 |
| ACTTGGTAAA | GGATGGACTA | CCCCACCCTA | CAAGGGGGT | TGGCAGCCAG | GTAGGCCCAT | 2940 |
| AAAGAGGCCC | CCTGAGGAGT | CCTCCTCATT | CTCTGCTCTT | CCTCCTCCGG | CACACATCGG | 3000 |
| ACCTAGTAGC | TGCTGAAACC | ATGGGCCTGG | GTGTCCTGTG | TCTGGC | | 3046 |

( 2 ) INFORMATION FOR SEQ ID NO:2:

( i ) SEQUENCE CHARACTERISTICS:
        ( A ) LENGTH: 3035 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| AAGCTTGTGT | GGTGGGACTA | TGTAGAGCTG | ACCCCTCCC | TGCAGCCCTG | CTAGACTCTG | 60 |
| AAGAGAGCCA | AGGCCAGTGG | GTAGGAGGAG | ACAGGTCTGG | AGCTGGTGCA | GAGAGAGGAA | 120 |
| TGAGCCCTGC | ATGGGTTTGA | TCAGAAACTC | AGCCTTGTGT | AGGGACACCC | TGGGGCCCGG | 180 |
| TGCTGTCCAT | GCATGACCTC | ACAGAAGCGC | AGAGCTGCCC | TCTCTACAGA | GGAGCGCCTG | 240 |
| ATTTGTGTGG | GAGCTAGGCA | GAGATCTGCA | TGCATGCGGA | GGAGCCAGGC | TTCAAGCCAG | 300 |
| CCTGGGGGAC | CCCAAGCGGG | ACTATCTCCC | CTTCTGCACC | TGGCTCTGGT | GTCTTCCCAC | 360 |
| TGTGGACCCA | GTGCCCTGCT | CACCCACCAC | ATTCATACCC | TGGAGTCCTG | GGTCCTCAGA | 420 |
| GATCCATGAC | ACTGCCTCAC | CCCCAACTTC | AAATTCTCTG | GGGCTCCACC | CGCTGGTCTC | 480 |
| AGCTACGTGA | AGCAGTCACC | GTAGACTAGA | GGGTATTTTT | TAGATTTAGG | TCACTCTATC | 540 |
| ATCCAGGCTG | GAGTGCAGTG | GCACAATCAT | AGCTCACTGC | AGCCTCGGCT | TCCTGGGCCC | 600 |
| AAGTGATCCT | CCCACCTCAG | CCTCCCCGAG | GATACGTGGT | TTTTTTTTC | TTTTTTCAGA | 660 |
| CAGGGTCTCA | CTCTGTCTCC | CAGGCTGGAG | TGCAGTGGTG | CGATCTTGGC | TCACTGCAGC | 720 |
| CTCCGCCTCC | CGGGTTCAAG | CCATTCTCCT | GCCTCAGCCT | CCTGAGTAGT | TGGGATCATA | 780 |

```
GGCATGCATC  ACCCCACCTG  GCTAATTTTT  GTATTTTTAG  TAGAGACGGG  GTTTTGCCAT      840
ATTGGCCAGG  CTAGTCCCTG  AGGATCATTT  TTTTTCCCC   GAGATGGAGT  CTCCCTCTGT      900
CGCCCAGGCT  GGAGTGCAAT  GGCAACCTTG  GCTCACTGCA  ACCTCCGCCT  CCCAGGTTCA      960
AGCAATTCTT  CTGCCTCAGC  TTCCCGAGTA  GTTGGGATTA  CAGGCATGCG  CCACCATGCC     1020
CAACTAATCT  TTGTATTTTT  ACTAGAGACA  GGGTTTCACC  ATGTTGGTCA  GGCTGGTCTT     1080
GAACACCTGA  CCTCAGGTTA  TCCACCCGCC  TCAGTCTCCC  AAAGTGCTGG  AGTTACAGGC     1140
GAGAGCCACT  GCGCCCAGCC  GAGGATACCT  TTTTTTTTT   TTTTAAGACA  GAATATCGCT     1200
CTGTTCCAGG  CTAAAGTGCA  AAGGCGTGAT  CTCGGCTCAC  TGCAACCTCC  GCCTCCCAGG     1260
TTCAAGCTGT  TCTTCTGCCT  CAGCCTCCCG  AGTAGCTGGG  ATTACAGGCG  CCTGCCACCA     1320
TGCCCTGCTA  ATTTTTGTAT  TTTTAGTAGA  GATGGGGTTT  CACCGTGTTG  GCCAGACTGG     1380
TCTCGAACTC  CTGACCTCGT  GATCCACCCG  CCTCAGCCTC  CCAAATGCTG  GGATTACAGA     1440
TGTGAGCCAC  CGCACCCGGC  CTGGCAGAGG  ATACTTTTTA  AGGTCAAAGA  CAGTAGCAGA     1500
GGTGGAGTTC  CTGGGAACAG  GGTCATGAGG  GGAAGAGGGG  GTTCGGAGGG  AGCGAGTAGC     1560
CACTGGCTAC  CTCTAGAAAG  GGAAGGCTTT  GGTGCAACAT  CGTTCCCCTG  CAGTTTTACT     1620
CATCTTTGCT  TCCTGCCCTT  TCATCATCCA  ATCGGGCAGG  CAGGACAGGG  CCTGAGGGGG     1680
CAGGGATCCA  GTGGGTGCCT  CTCTAGACTA  ACCCCAGCTC  AGGACTCCCA  GAGCCCCTTC     1740
CCTGAGGCCC  TGCTGCCCCC  AAGCCCAGAT  TGGGGATCCC  AAGCAGCACG  TAGGCAGAGC     1800
CAGTGAGGTC  CCCGTTAGTC  CCATTGAAAG  CTCTAAAACC  AGCGAACCCT  CAGTCCAGCC     1860
TCAGGTCAGG  CATCCAGGAC  GCCCTCAGCC  TCATGGGTGA  GCCATCTCTG  CGGACACTGC     1920
ACAGGGCCTA  CGATCCATCG  CTGCCTCCCG  AGGATGCCAG  CCAGGCCCCC  GTTGAGATAA     1980
CTGCTTCCCT  GCTGGACAAG  GCTGGGACCA  GCCATCTCGG  TGACAGTTCC  AGAACCCTG     2040
GCCTGGGCTG  CTGGGTTCAA  TGGAAAAAGG  CTGTGACTAG  AGTCAGGGGG  ATGGTCTCAG     2100
TGACCTCAAG  GATAAGGCCA  GATCCTTGCA  CTGTCAGTGA  CCCAAAGCAA  CAGGTGTCCA     2160
GAGCAGCAGT  GTGGCGCCTT  CACGCCCCCA  CACATCAGCC  CAACTCACCC  AGGACAGGA     2220
CTGTAGCCTC  AGCACTCAAC  CCATGTGCCC  TGTGTGGGGT  CTCTTCCCAC  TGCACTCACA     2280
GGAGAGGAAG  GGTCCCTCAG  GGGTCCACTG  GGGTCCCCTC  CTGCAAATGG  GGCAAGGAGA     2340
GGGGCAAGGG  GCTGTCTCAA  GGCCCCTGGA  GCACATGCAG  GTCCTGGACT  GGGGCTCCTG     2400
GGAGGGCCAT  GATTCTGGGC  TCCATGAGTT  CAGAGCAGAC  GCCTTGTTTT  TCCTTGTCCA     2460
CTGTCAGCCA  CCCCACCCTT  CCCTGACCCT  TAAAAGAACC  AGGAAACAGC  ACATGATCTG     2520
TTGGAAGGAG  GCATTCATTC  TTTCCTTTCT  GTGGGTGTGG  GGAGGGACCA  CAGGGCACAT     2580
ACCCCACCCT  GGGATCCAGC  TGAGCAGGGG  GGTCAGAGAT  GACAGCTCTT  CCGGCTCACA     2640
GGCCACCGGC  CCACATACAG  GGCAATCAGA  AGAAAGAAAC  AGCACAAGGA  AGGCACAGAG     2700
GGAGTCGTTG  TCCCTGCCAG  AGGTGCAGCA  CTCCGGGAAT  GTCCCTCACT  CTCCCCGTCC     2760
CTCTGTCTTG  CCCAATCCTG  ACCAGGTGCA  GAAATCTTGC  CAAGTGTTTC  CGCAGGAGTT     2820
GCTGGCAATT  GCCTCACATT  CCTGGCCTTG  GCAAAGAATG  AATCAACCCA  CCCTAGATCC     2880
CATAAATAGG  GCCACCCAGG  TGAGCCTCTC  ACTCGCCACC  TCCTCTTCCA  CCCCTGCCAG     2940
GCCCAGCAGC  CACCACAGCG  CCTCCTTCCT  CGGCCCTGAA  ATCATGCCCC  TAGGTCTCCT     3000
GTGGCTGGGC  CTAGCCCTGT  TGGGGCTCTG  CATGC                                  3035
```

( 2 ) INFORMATION FOR SEQ ID NO:3:

( i ) SEQUENCE CHARACTERISTICS:
  ( A ) LENGTH: 827 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:3:

| | | | | | | |
|---|---|---|---|---|---|---|
| CTCCTCCTGC | ACACCTTCCG | CACACCTCCC | TCGCTCTCCC | ACACCACTGG | CACCAGGCCC | 60 |
| CGCACACCTG | CTCGGCTGCA | GGAGAATGGC | TACTCATCAC | ACGCTGTGGA | TGGGACTGGT | 120 |
| CCTGCTGGGG | CTGCTGGGCG | CCTACAGGC | AGCACCCGAG | GCCCAGGTCT | CCGTGCAGCC | 180 |
| CAACTTCCAG | CCGGACAAGT | TCCTGGGGCG | CTGGTTCAGC | GCGGGCCTCG | CCTCCAACTC | 240 |
| GAGCTGGCTC | CAGGAGAAGA | AGGCAGCGCT | GTCCATGTGC | AAGTCGGTGG | TGGCCCCTGC | 300 |
| GGCGGATGGT | GGCTTCAACC | TGACCTCCAC | CTTCCTCAGG | AAAAACCAGT | GTGAGACCCG | 360 |
| AACCATGCTG | CTGCAGCCCG | GGACTCCCT | CGGCTCCTAC | AGCTACCGGA | GTCCCACTG | 420 |
| GGGCAGCACC | TACTCTGTGT | CAGTGGTGGA | GACTGACTAC | GACCACTACG | CCCTGCTGTA | 480 |
| CAGCCAGGGC | AGCAAGGGCC | CCGGCGAGGA | CTTCCGCATG | GCCACCCTCT | ACAGCCGAAC | 540 |
| CCAGACCCCC | AGGGCTGAGT | TAAAGGAGAA | ATTTACCGCC | TTCTGCAAGG | CCCAGGGCTT | 600 |
| CACAGAGGAT | TCCATTGTCT | TCCTGCCCCA | AACCGATAAG | TGCATGACGG | AACAATAGGA | 660 |
| CTCCCCAGAG | CTGAAGCTGG | GACCGCAGCC | AGCCAGGTGA | CCCCTGCGAT | CTGGATGTTT | 720 |
| CCGCTCTGTT | CCTTCCCCGA | GCCCCTGCCC | CGGCTCCCCG | CCAAAGCACC | CCTGCCCCCT | 780 |
| CGGGCTTCCT | CCTGGCTCTG | CGGAATAAAC | TCCGGAAGCA | AGTCTGT | | 827 |

( 2 ) INFORMATION FOR SEQ ID NO:4:

( i ) SEQUENCE CHARACTERISTICS:
  ( A ) LENGTH: 759 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:4:

| | | | | | | |
|---|---|---|---|---|---|---|
| CCTCAGGCTC | AGACACCTGC | TCTACTCCAA | GCAAATGGCT | GCTCTTCCAA | TGCTGTGGAC | 60 |
| CGGGCTGGTC | CTCTTGGGTC | TCTTGGGATT | TCCACAGACC | CCAGCCCAGG | GCCATGACAC | 120 |
| AGTGCAGCCC | AACTTTCAAC | AAGACAAGTT | CCTGGGGCGC | TGGTACAGCG | CGGGCCTCGC | 180 |
| CTCCAATTCA | AGCTGGTTCC | GGGAGAAGAA | AGAGCTACTG | TTTATGTGCC | AGACAGTGGT | 240 |
| AGCTCCCTCC | ACAGAAGGCG | GCCTCAACCT | CACCTCTACC | TTCCTAAGGA | AAAACCAGTG | 300 |
| TGAGACCAAG | GTGATGGTAC | TGCAGCCGGC | AGGGGTTCCC | GGACAGTACA | CCTACAACAG | 360 |
| CCCCCACTGG | GGCAGCTTCC | ACTCCCTCTC | AGTGGTAGAA | ACCGACTACG | ATGAGTACGC | 420 |
| GTTCCTGTTC | AGCAAGGGCA | CCAAGGGCCC | AGGCCAGGAC | TTCCGCATGG | CCACCCTCTA | 480 |
| CAGCAGAGCC | CAGCTTCTGA | AGGAGGAACT | GAAGGAGAAA | TTCATCACCT | TAGCAAGGA | 540 |
| CCAGGGCCTC | ACAGAGGAGG | ACATTGTTTT | CCTGCCCCAA | CCGGATAAGT | GCATTCAAGA | 600 |
| GTAAACACAG | GTGAGAGAAG | TCAGTCACAG | GTAACACATG | GTGATGTGGC | CTCAGGACTC | 660 |
| CCGTGCTCTG | TCACTCTTGA | GACCCAAGCC | CTGGCTCCCC | AAAGACTTC | TCCGCCCTCC | 720 |
| AGCTTTGCCT | TGGTGGAGAA | ATAAAATCCA | AAGCAAGTC | | | 759 |

( 2 ) INFORMATION FOR SEQ ID NO:5:

(i) SEQUENCE CHARACTERISTICS:
(A) LENGTH: 876 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:5:

| | | | | | | |
|---|---|---|---|---|---|---|
| CTCTTCCTCC | TCCGGCACAC | ATCGGACCTA | GTAGCTGCTG | AAACCATGGG | CCTGGGTGTC | 60 |
| CTGTGTCTGG | CCCTTGTCCT | GCTTGGGGTC | CTGCAGAGGC | AGGCCCAGGA | CTCAACTCAG | 120 |
| AACTTGATCC | CTGCCCCACC | TCTGATCAGT | GTGCCCCTGC | AGCCAGGCTT | CTGGACCGAA | 180 |
| CGGTTCCAGG | GCAGGTGGTT | CGTTGTCGGC | CTGGCAGCGA | ATGCGGTCCA | GAAAGAAAGA | 240 |
| CAAAGCCGCT | TTACCATGTA | CAGCACCATC | TATGAGCTAC | AGGAAGACAA | TAGCTACAAC | 300 |
| GTCACTTCCA | TCCTCGTCAG | GGGCCAGGGC | TGTCGCTACT | GGATCAGAAC | ATTCGTTCCA | 360 |
| AGCTCCAGGC | CTGGCCAGTT | CACCCTGGGG | AATATTCACA | GCTACCCTCA | GATACAGAGC | 420 |
| TACGATGTGC | AAGTGGCCGA | CACTGACTAC | GACCAGTTTG | CCATGGTATT | TTTCCAGAAG | 480 |
| ACCTCTGAAA | ACAAACAGTA | CTTCAAAGTC | ACCCTGTACG | GAAGAACCAA | GGGGCTGTCC | 540 |
| GATGAACTGA | AGGAGCGATT | CGTCAGCTTT | GCCAAGTCTC | TGGGCCTCAA | GGATAACAAC | 600 |
| ATCGTTTTCT | CTGTTCCAC | CGACCAATGC | ATTGACAACT | GAACAGACGG | TGAGCGTGGC | 660 |
| TGACTGGGAT | GTGCAGTGGC | CTGATGGTTC | AGGTCCCACC | TGTCTGTCTG | CCGCTCCATC | 720 |
| TTTCCTGTTG | CCAGAGAATC | ACCTGGCTGC | CCCACCAGCC | ATGATTCCAT | CAAGCATCTG | 780 |
| ATCCCTCTTA | TTTGATCAGC | TCTCCCCATC | CACCTGTGTT | AACGCTGCCC | CACCAACGGG | 840 |
| CTCCCCCTTT | CTGCTGAATA | AACACATGTC | CCCAAA | | | 876 |

(2) INFORMATION FOR SEQ ID NO:6:

(i) SEQUENCE CHARACTERISTICS:
(A) LENGTH: 660 base pairs
(B) TYPE: nucleic acid
(C) STRANDEDNESS: double
(D) TOPOLOGY: linear (ii) MOLECULE TYPE: cDNA (xi) SEQUENCE DESCRIPTION: SEQ ID NO:6:

| | | | | | | |
|---|---|---|---|---|---|---|
| CACGAGTCCA | CCCCTGCCAG | GCCAGCAGC | CACCACAGCG | CCTGCTTCCT | CGGCCCTGAA | 60 |
| ATCATGCCCC | TAGGTCTCCT | GTGGCTGCCT | AGCCTGTTGG | GGGCTCTGCA | TGCCCAGGCC | 120 |
| CAGGACTCCA | CCTCAGACCT | GATCCCAGCC | CCACCTCTGA | GCAAGGTCCC | TCTGCAGCAG | 180 |
| AACTTCCAGG | ACAACCAATT | CCAGGGGAAG | TGGTATGTGG | TAGGCCTGGC | AGGGAATGCA | 240 |
| ATTCTCAGAG | AAGACAAAGA | CCCGCAAAAG | ATGTATGCCA | CCATCTATGA | GCTGAAAGAA | 300 |
| GACAAGAGCT | ACAATGTCAC | CTCCGTCCTG | TTTAGGAAAA | AGAAGTGTGA | CTACTGGATC | 360 |
| AGGACTTTTG | TTCCAGGTTG | CCAGCCCGGC | GAGTTCACGC | TGGGCAACAT | TAAGAGTTAC | 420 |
| CCTGGATTAA | CGAGTTACCT | CGTCCGAGTG | GTGAGCACCA | ACTACAACCA | GCATGCTATG | 480 |
| GTGTTCTTTA | AGAAAGTTTC | TCAAAACAGG | GAGTACTTCA | AGATCACCCT | CTACGGGAGA | 540 |
| ACCAAGGAGC | TGACTTCGGA | ACTAAAGGAG | AACTTCATCC | GCTTCTCCAA | ATCTCTGGGC | 600 |
| CTCCCTGAAA | ACCACATCGT | CTTCCCTGTC | CCAATCGACC | AGTGTATCGA | CGGCTGAGTG | 660 |

(2) INFORMATION FOR SEQ ID NO:7:

(i) SEQUENCE CHARACTERISTICS:
(A) LENGTH: 15 base pairs ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:7:

CACCATCTAT GAGCT 15

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:8:

CACCATCTAT GAGCT 15

( 2 ) INFORMATION FOR SEQ ID NO:9:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:9:

GGAGGTCGAA CTCAGA 16

( 2 ) INFORMATION FOR SEQ ID NO:10:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:10:

CGACTGTGCA TGTCCA 16

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:11:

GGCAATTGCC 10

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:12:

GGCAATTACC                                                                                          10

( 2 ) INFORMATION FOR SEQ ID NO:13:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:13:

GGCAATTACT                                                                                          10

( 2 ) INFORMATION FOR SEQ ID NO:14:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:14: